United States Patent [19]
Hegde et al.

[11] Patent Number: 5,725,535
[45] Date of Patent: Mar. 10, 1998

[54] MULTIPLE BALLOON STENT DELIVERY CATHETER AND METHOD

[76] Inventors: Anant V. Hegde, 36105 Toulouse St., Newark, Calif. 94560; Deepak R. Gandhi, 911 Bowen Ave., San Jose, Calif. 95123; Thomas Bourne, 2650 California St., Apt. 96, Mountain View, Calif. 94040; James R. Kermode, 1080 Kildare Ave., Sunnyvale, Calif. 94087

[21] Appl. No.: 717,299

[22] Filed: Sep. 20, 1996

[51] Int. Cl.$^6$ .................................................. A61F 11/00
[52] U.S. Cl. ........................... 606/108; 604/96; 606/198
[58] Field of Search ............................... 606/108, 191, 606/198, 194, 195; 604/96, 101

[56] References Cited

U.S. PATENT DOCUMENTS

| | | | |
|---|---|---|---|
| 5,226,889 | 7/1993 | Sheiban | 604/101 |
| 5,456,694 | 10/1995 | Marin et al. | 604/96 |
| 5,632,760 | 5/1997 | Sheiban et al. | 604/96 |

*Primary Examiner*—Michael Buiz
*Assistant Examiner*—Kevin Truong
*Attorney, Agent, or Firm*—Flehr Hohbach Test Albritton & Herbert LLP

[57] ABSTRACT

A multiple balloon catheter for use in a vessel of a patient and for use with an inflation/deflation device. A flexible elongate tubular member with proximal and distal extremities has a distal balloon mounted on the distal extremity of the flexible elongate tubular member. Coaxial inner and outer balloons are mounted on the distal extremity of the flexible elongate member proximal of the distal balloon. The flexible elongate tubular member has balloon inflation lumens therein in communication with the interiors of the distal balloon and the inner and outer coaxial balloons. A manifold is secured to the proximal extremity of the flexible elongate tubular member in communication with the inflation lumens and is adjusted to be coupled to the inflation/deflation device. Valves are carried by the inflation/deflation manifold for inflating the distal balloon in the inner and outer coaxial balloons one at a time or in unison without removal of the inflation/deflation device from the manifold.

13 Claims, 3 Drawing Sheets

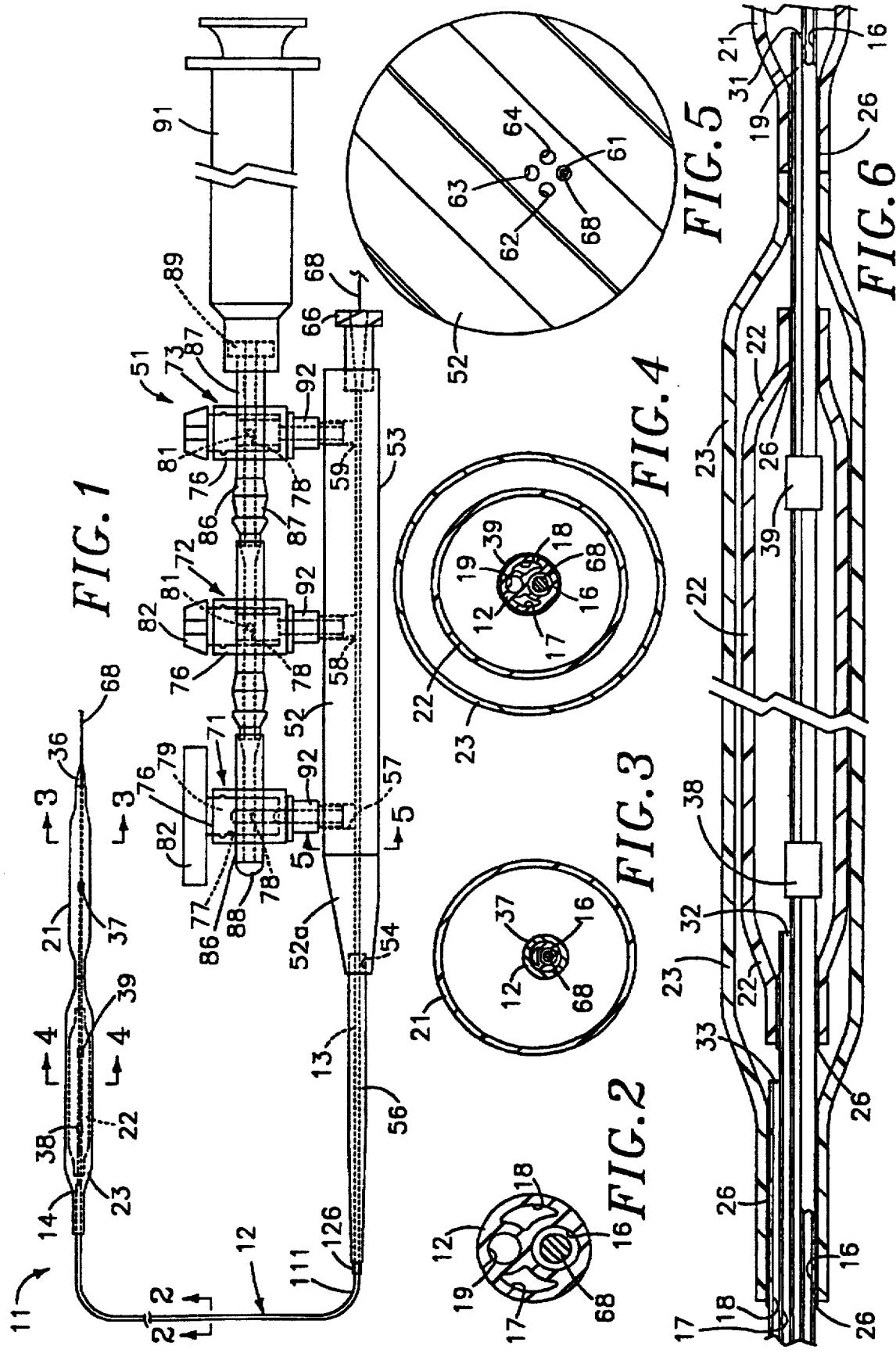

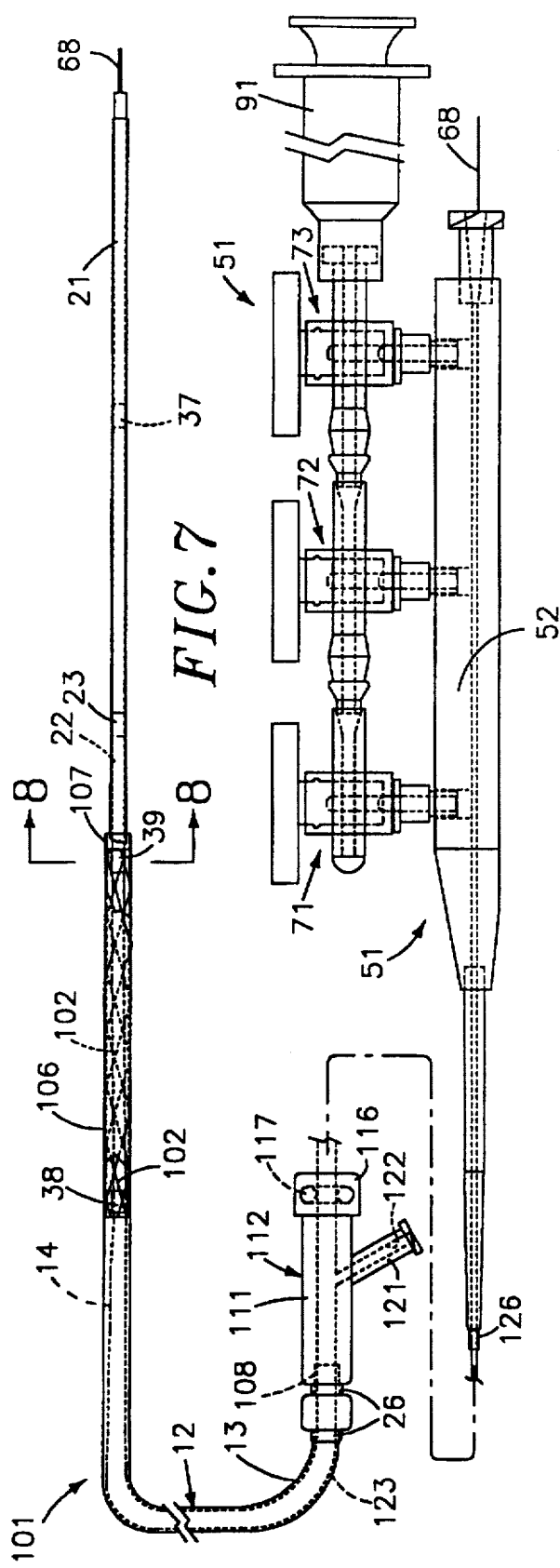

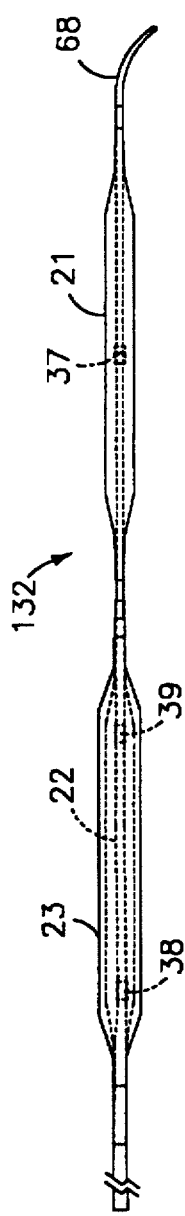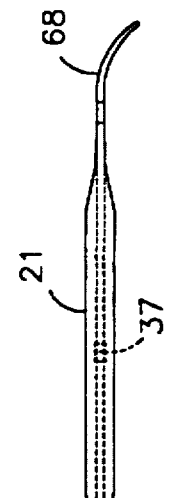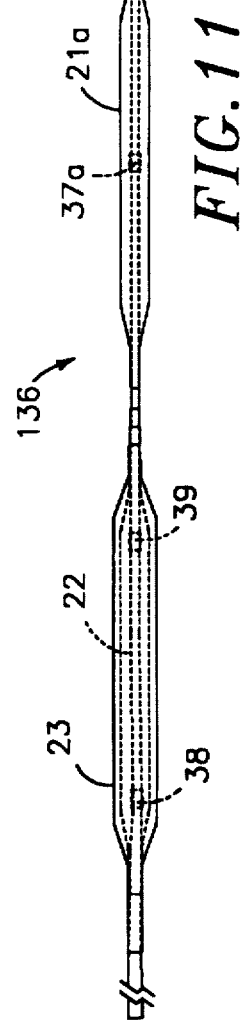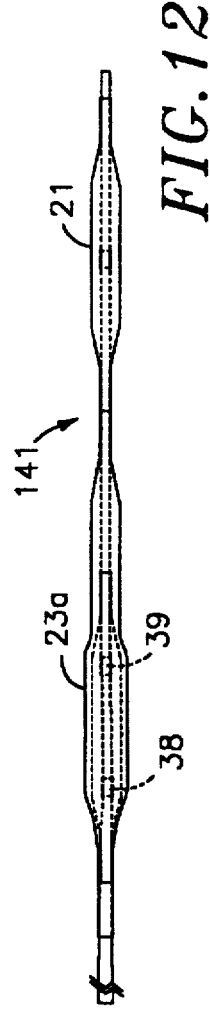

MULTIPLE BALLOON STENT DELIVERY CATHETER AND METHOD

This invention relates to a multiple balloon stent delivery catheter and method for deploying the same in vessels of humans.

Heretofore stents have been delivered into vessels in the human body as for example arterial vessels in the heart. In delivering a stent to a lesion in such an arterial vessel, it has been the practice to first cross the lesion with a guide wire followed by a dilatation balloon catheter after which the dilatation balloon is inflated to dilate the lesion. The balloon is then deflated and the balloon catheter removed along with the guide wire. Thereafter, another guide wire is advanced through the stenosis. A stent delivery catheter is then advanced over this guide wire until the stent is disposed within the stenosis. Thereafter, the balloon of the stent delivery catheter is inflated to expand the stent into engagement with the stenosis after which the balloon is deflated and the balloon stent delivery catheter is withdrawn. Often a high pressure balloon is then advanced into the stent and inflated to more snugly secure the stent against the arterial wall. Thereafter, the high pressure balloon is deflated and the high pressure balloon catheter and the guide wire are removed from the vessel. It has been found that such a procedure is time consuming and in addition requires the use of many different devices which require many insertions into the patient and removals of such devices from the patient. There is therefore need for a new and improved medical device for delivering stents and a method which overcomes these difficulties.

In general, it is an object of the present invention to provide a multiple balloon stent delivery catheter and method which makes it possible to deliver a stent to a desired location with a minimum number of devices inserted into and removed from the patient.

Another object of the invention is to provide a multiple balloon stent delivery catheter which can perform multiple functions.

Another object of the invention is to provide a multiple balloon stent delivery catheter in which a manifold is provided making it possible to inflate the multiple balloons one at a time or in unison without removing the catheter from the patient.

Another object of the invention is to provide a multiple balloon stent delivery catheter of the above character which makes it possible to attain different diameters for dilations of stenoses.

Another object of the invention is to provide a multiple balloon stent delivery catheter in which multiple diameter sized balloons are provided on a single catheter eliminating the need for catheter exchanges.

Another object of the invention is to provide a multiple balloon stent delivery catheter having tapered balloons.

Another object of the invention is to provide a multiple balloon stent delivery catheter of the above character in which various balloon profiles can be provided.

Additional objects and features of the invention will appear from the following description in which the preferred embodiments are set forth in detail in conjunction with the accompanying drawings.

FIG. 1 is a side-elevational view of a multiple balloon catheter and a manifold for use with the same.

FIG. 2 is an enlarged cross-sectional view taken along the line 2—2 of FIG. 1.

FIG. 3 is an enlarged cross-sectional view taken along the line 3—3 of FIG. 1.

FIG. 4 is an enlarged cross-sectional view taken along the line 4—4 of FIG. 1.

FIG. 5 is an enlarged cross-sectional view taken along the line 5—5 of FIG. 1.

FIG. 6 is an enlarged partial view in section of the coaxial balloons shown in FIG. 1.

FIG. 7 is a side-elevational view of a multiple balloon stent delivery catheter and manifold for use with the same.

FIG. 8 is an enlarged cross-sectional view taken along the line 7—7 of FIG. 7.

FIG. 9 is a cross sectional view similar to that shown in FIG. 7 but showing the outer balloon inflated to place the stent.

FIGS. 10, 11, 12, and 13 are side-elevational views of additional embodiments of multiple balloon catheters incorporating the present invention.

In general, the multiple balloon catheter is for use in the vessel of a patient with an inflation/deflation device. It is comprised of a flexible elongate tubular member having proximal and distal extremities. A distal balloon is mounted on the distal extremity of the flexible elongate tubular member. Coaxial inner and outer balloons are mounted on the distal extremity of the flexible elongate member proximal of the distal balloon. The flexible elongate tubular member has balloon inflation lumens therein in communication with the interiors of the distal balloon and the inner and outer coaxial balloons. An inflation manifold is secured to the proximal extremity of the flexible elongate tubular member and is in communication with the inflation lumens and is adapted to be connected to the inflation/deflation device. Valve means is carried by the inflation/deflation manifold for inflating the distal balloon in the inner and outer coaxial balloons one at a time or in unison without removal of the inflation/deflation device.

More in particular as shown in FIGS. 1 through 5 of the drawings, the multiple balloon catheter 11 consists of a flexible elongate tubular member 12 having proximal and distal extremities 13 and 14 serving as a shaft for the multiple balloon catheter 11. The flexible elongate tubular member 12 is formed of a suitable lubricous plastic such as Nylon or a copolymer of Nylon such as Pebax or other high lubricous materials such as polyethylene. Nylon 11 has been found to be a particularly suitable material. Other Nylons such as Nylon 12 or Nylon 66 can be utilized. The diameter of the shaft can be of a suitable size such as 3-French corresponding to 0.039" of the outside diameter. The shaft 12 has a suitable length ranging from 130 to 175 centimeters and typically approximately 150 centimeters when used for angioplasty. The flexible elongate tubular member or shaft 12 is typically an extrusion and is provided with a plurality of extruded lumens therein. Thus, as shown in FIG. 2 the shaft 12 is provided with a guide wire lumen 16 which is sized to receive a conventional guide wire 68, as for example one having a diameter of 0.014", and thus is provided with a diameter of 0.017". The shaft is also provided with three balloon inflation lumens, 17, 18 and 19 in which lumen 17 and 18 are generally crescent- shaped and lumen 19 is generally circular in cross section. A plurality of inflatable balloons is provided on the distal extremity 14 of the flexible elongate tubular member 12. Thus, as shown in FIG. 1, there is provided a distal balloon 21, an inner balloon 22 which is proximal of the distal balloon 21, and an outer balloon 23 which is coaxial with the inner balloon 22. The balloons 21, 22 and 23 are formed of a non-compliant or low-compliant high pressure material which is capable of withstanding pressures in the range of 18 to 20 atmospheres. Such high strength balloon materials typically incorporate materials such as Nylon 12 or Nylon 11. The distal balloon 21 can have a diameter ranging from 1.5 to 3 millimeters and typically approximately 2 millimeters. The inner balloon 22 can have a diameter ranging from 2.0 to 4.0 millimeters and typically 2.5 or 3 millimeters, whereas the outer balloon 23 can have a diameter ranging from 2.5 to 5 millimeters and typically 3 millimeters to 3.5 millimeters. The balloons can have a wall thickness ranging from 0.0005" to 0.0015" and preferably a thickness of approximately 0.00075". The balloons 21, 22 and 23 can have a suitable working length, as for example the distal balloon 21 can have a working length of 20 millimeters, the inner balloon 22 a working length of 20 millimeters and the outer balloon 23 a working length of 22 millimeters. It should be appreciated that the balloons, if desired, can have increased or decreased lengths as desired. The balloons 21, 22 and 23 are bonded in appropriate locations on the distal extremity 14 of the flexible elongate tubular member 12 in a suitable conventional manner as for example by the use of an adhesive, heat bonding or solvent bonding to form fluid tight seals so that the balloons can be inflated. Thus as shown in FIGS. 3 and 4, an adhesive 26 has been provided for securing the extremities of the balloons 21, 22 and 23 to the distal extremity 14 of the flexible elongate member 12. Thus, as shown in partial view in FIG. 6, an adhesive 26 is utilized for making these bonds. The flexible elongate extremity 14 is also provided with holes of ports establishing communication with the balloon inflation lumens and the interior of the associated balloons. Thus there is provided an opening or port 31 establishing communication between the interior of the distal balloon 21 and lumen 19. Similarly, there is provided an opening or port 32 establishing communication between the lumen 17 and the interior of the inner balloon 22. A port 33 establishes communication between the lumen 18 and the interior of the outer balloon 23. A soft atraumatic tip 36 is provided on the distal extremity 14 and is secured thereto by suitable means such as adhesive (not shown). The tip can be formed of a soft plastic material as for example Pebax.

Radiopaque markers are provided on the distal extremity 14 of the flexible elongate tubular member 12 to aid in locating the positions of the balloons 21, 22 and 23 during use and consist of a radiopaque marker 37 mounted on the flexible elongate tubular member 12 equidistant between the ends of the distal balloon 21. A pair of markers 38 and 39 is also provided on the distal extremity of the flexible elongate tubular member 12 proximal of the marker 37 and spaced apart near the opposite ends of the inner balloon 22. The radiopaque markers can be formed of a suitable radiopaque material such as gold or platinum. By placing two radiopaque markers in the inner balloon 22 and a single radiopaque marker on the distal balloon 21, it is easy to differentiate the distal balloon 21 from the proximal coaxial balloons 22 and 23.

A manifold assembly 51 is secured to the proximal extremity 13 of the flexible elongate tubular member 12 which can be utilized for inflating and deflating the balloons individually without having to disconnect and reconnect an inflation/deflation device 91. The manifold assembly 51 consists of an elongate cylindrical body 52 formed of a suitable material such as polycarbonate plastic which is provided with a flat 53 so that the manifold assembly 51 will remain in an upright position when resting on a flat surface. The body 52 is provided with a tapered or cone-shaped distal extremity 52a which has a bore 54 therein which has the proximal extremity 13 of the flexible elongate tubular member 12 sealed therein and bonded therein by suitable means such as an adhesive (not shown). A strain relief sleeve 56 is provided on the proximal extremity 13. The manifold body 52 is provided with spaced-apart balloon inflation chambers, namely a distal balloon chamber 57, an inner balloon chamber 58 and an outer balloon chamber 59. The inner balloon chamber 58 is disposed proximally of the distal balloon chamber 57 and the outer balloon chamber 59 is disposed proximally of the inner balloon chamber 58. The body 52 is provided with a plurality of longitudinally extending bores. Thus, as shown in FIG. 5, there is provided a guide wire bore 61 in alignment with the guide wire lumen 16 in the flexible elongate tubular member 12. Similarly, there are provided balloon inflation bores 62, 63 and 64 in communication with balloon inflation lumens 17, 18 and 19 respectively. The chambers 57, 58 and 59 are in communication, respectively, with the bores 64, 63 and 62.

A Luer fitting 66 is mounted on the body 52 and is in communication with the guide wire bore 61 to provide a guide wire port which, as shown, has a guide wire 68 disposed therein. The guide wire 68 is of a conventional type such as an 0.014" diameter guide wire. A Tuohy-Borst adapter (not shown) typically is carried by the Luer fitting 66 to prevent blood from seeping around the guide wire while the catheter 11 is in use.

The manifold assembly 51 includes means for supplying an inflation fluid to the chambers 57, 58 and 59 and consists of valve assemblies 71, 72 and 73 connected, respectively, to the chambers 57, 58 and 59. Each of the valve assemblies 71, 72 and 73 consist of a cylindrical valve body 76 having a bore 77 therein and another bore 78 extending transversely therethrough. A stem 79 is rotatably mounted in the bore 77 and has a bore 81 extending transversely therethrough and adapted to be moved into and out of registration with the bore 78 in the valve body 76. A handle 82 is provided on the stem 79. Each valve body 76 is connected to adjacent valve body 76. Thus as shown each valve body 76 is provided with a male fitting 86 and a female fitting 87 in communication with the transverse bore 78 in the valve body 76. As shown in FIG. 1, the male fitting 86 on one valve body 76 mates with the female fitting 87 of the adjacent valve body 76 so that a fluid communication channel is established between the valve assemblies 71, 72 and 73. The most distal male fitting 86 is truncated and is plugged with a plug 88. A Luer fitting 89 is provided on the most proximal female fitting 87 and has mounted thereon a conventional ENDOFLATER™ or syringe 91. Each valve assembly 71, 72 and 73 also includes a coupling 92 which couples the bore 77 into the respective chambers 57, 58 and 59.

With such a manifold assembly, balloons 21, 22 and 23 can be inflated and deflated individually or can be inflated simultaneously as desired merely by operation of the valve assemblies 71, 72 and 73 in an appropriate manner as hereinafter described. Thus, for example, if it is desired to inflate only the distal balloon 21, all of the valve assemblies 71, 72 and 73 are turned to the closed position. The valve assembly 71 is then rotated by 90° to turn it to an open position as shown in FIG. 1, after which an inflation/deflation device 91 is operated to introduce an inflation fluid chamber 57 and then into the bore 64 and into the lumen 19 for inflating the distal balloon 21. The balloon 21 can also then be deflated. If that is not desired, the valve assembly 71 can be turned another 90° to close it to prevent deflation of the balloon 21 or, alternatively, to deflate the balloon 21 and hold it uninflated, after which the catheter 11 can be moved as hereinafter described and the next balloon, as for example inner balloon 22 can be inflated by rotating the valve 72 to the open position. Thereafter in a similar manner, the outer balloon 73 can be inflated.

Also incorporating the present invention is a multiple balloon stent delivery catheter 101 which is shown in FIG. 7. This multiple balloon stent delivery catheter 101 is very similar to the multiple balloon catheter 11 hereinbefore described. It consists of a flexible elongate tubular member 12 having proximal and distal extremities 13 and 14 with a distal balloon 21 and inner and outer balloons 22 and 23. A balloon expandable stent 102 is frictionally mounted on the coaxial inner and outer balloons 22 and 23. As shown in FIG. 8, the balloons 22 and 23 are not inflated and the balloon expandable stent 102 is frictionally secured to the outer balloon 23 sufficiently tightly so that a force in excess of approximately one-half pound is required to remove the stent 102 from the outer balloon 23. Such a frictional force is desirable in order to prevent inadvertent displacement of the stent 102 from the outer balloon 23 during deployment. The balloon stent 102 can be of any conventional type and can be formed of a suitable material such as stainless steel or a nickel titanium alloy. A stent of desired length can be provided. Also if desired, stents can be provided in tandem on the outer balloon 23.

As shown, the stent 102 is positioned relative to the radiopaque markers 38 and 39 so that the positioning of the stent can be precisely ascertained during deployment as hereinafter described.

Means is provided for covering the stent 102 until it has been deployed and consists of a sheath 106 and can be formed of a very thin molded plastic having a lubricous outer surface such as one made of Teflon. The sheath 106 can have a single wall thickness ranging from 0.001" to 0.005" and preferably a wall thickness of approximately 0.0015". The sheath 106 should have a wall thickness which will resist elongation while being withdrawn as hereinafter described. The sheath 106 has a distal extremity 107 which extends slightly beyond the distal extremity of the balloon expandable stent 102, as for example a distance of approximately 1 millimeter. The sheath 106 then extends proximally over the flexible elongate tubular member shaft 12 to the proximal extremity 13 thereof. The proximal extremity 108 of the sheath 106 is secured to a cylindrical fitting 111 forming a part of a hemostasis valve assembly 112. The hemostasis valve assembly 112 includes an internally threaded cap 116 which is threadedly mounted on the cylindrical fitting 111 and engages an O-ring 117 to form a liquid-tight seal between the fitting 111 and the proximal extremity 13 of the flexible elongate member 12. A Luer-type fitting 121 in the form of a side arm is secured to the fitting 111 and provides a port 122 for introducing a flushing saline liquid which can pass into the annular space 123 between the exterior of the flexible elongate tubular member or shaft 12 over the outer balloon 23 within the sheath 106 and exiting out the distal extremity 107 of the sheath 106 to be utilized for a purpose hereinafter described.

A marker 126 visible to the human eye formed of a suitable material such as a paint or a colored tape is provided on the proximal extremity 13 of the flexible elongate tubular member 12 proximal of the hemostasis valve assembly 112. The spacing between the proximal extremity of the hemostasis valve assembly 112 and the marker 126 should be a distance at least equal to or slightly greater than the length of the stent 102 so that when the threaded cap 116 is loosened, the fitting 111 can be retracted to pull with it the sheath 106. When the threaded cap 116 is adjacent to or overlies the marker 126, the sheath 106 will have cleared the stent 102 to permit placement of the stent 102 as hereinafter described.

A manifold assembly 51 is provided which is substantially identical to the manifold assembly 51 hereinbefore described.

Operation and use of the multiple balloon catheter 11 may now be briefly described as follows. Let it be assumed that it is desired to perform a balloon angioplasty procedure to enlarge an opening in a stenosis in an arterial vessel of the heart of a human patient. The femoral artery of the patient is accessed in a conventional manner by advancing the guide wire 68 until it extends through the stenosis. Thereafter, the multiple balloon catheter 11 is inserted into the femoral artery utilizing the guide wire 68 as a guide to advance the distal extremity 14 of the flexible elongate tubular member 12 so that the distal balloon 21 is disposed within the stenosis. As soon as this has been accomplished by observation of the marker 37 under fluoroscopy, the distal balloon 21 can be inflated by rotating the valve 71 to an open position and then introducing a suitable inflation medium such as a contrast medium to inflate the balloon to its maximum diameter and to cause a flow passage of increased size to be created in the stenosis. After this has been accomplished, the distal balloon 21 is deflated by removing the inflation medium using the inflation/deflation device or syringe 91. After this larger opening has been formed in the stenosis by the distal balloon 21, the distal extremity 14 of the flexible elongate tubular member 12 is then further advanced into the stenosis until the coaxial inner and outer balloons 22 and 23 are positioned within the stenosis. This again can be visualized by observing the positioning of the markers 38 and 39 under fluoroscopy. The valve assembly 71 is then turned to a closed position and the valve assembly 72 is turned to an open position and an inflation medium is introduced into the inner balloon 22 which moves the outer uninflated balloon 23 into engagement with the stenosis to cause a larger size opening to be formed in the stenosis. If a still larger size opening is desired in the stenosis, the valve 73 can be turned to an open position and the outer balloon 23 can be inflated with a contrast medium or other suitable fluid. After a suitable dilation of the stenosis has occurred, the outer and inner balloons 23 and 22 can be deflated by withdrawing the inflation medium. The multiple balloon catheter 11 and the guide wire 68 can be removed from the femoral artery and the femoral artery closed surgically in a conventional manner. From the foregoing, it can be seen that all three of the balloons 21, 22 and 23 can be inflated individually or, alternatively, can be inflated in unison if desired without removal of the inflation/deflation device 91. This is made possible by use of the manifold assembly 51.

Operation and use of the multiple balloon stent delivery catheter 101 may now be briefly described as follows. Assuming that the multiple balloon stent delivery catheter 101 has been assembled as shown in FIG. 7 with the stent 102 in place and with the sheath 106 overlying the same, let it be assumed that it is desired to treat a stenosis occurring in an arterial vessel of the heart of the human patient. This vessel typically is accessed through the femoral artery of the patient. A guide wire 68 is introduced into the femoral artery in a conventional manner and is advanced until its distal extremity has passed through the stenosis. Thereafter, the multiple balloon stent delivery catheter 101 is advanced over the guide wire 68 until the small distal balloon 21 has been advanced into registration with the stenosis by observation of the marker 37. As soon as this has been accomplished, the valve 71 is opened and an inflation medium is introduced through the manifold 51 with the valves 72 and 73 in closed positions to inflate the distal balloon 21 to increase the size of the flow passage through the stenosis. After this has been accomplished, the distal balloon 21 is deflated. The distal extremity 14 of the multiple balloon stent delivery catheter 101 is advanced until the coaxial inner and outer balloons 22 and 23 are disposed within the stenosis by observation of the spaced apart markers 38 and 39. When this has occurred, the stent 102 is also positioned within the stenosis as well as the distal extremity 107 of the sheath 106.

After these desired procedures have been accomplished, the position of the stent 102 is again verified. If it is desired to change the position of the stent 102, the distal extremity 14 of the multiple balloon stent delivery catheter 101 can be changed after which the distal balloon 21 can be again inflated in the vessel to serve as an anchor for the distal extremity 14 of the flexible elongate tubular member 12. Thereafter, the sheath 106 can be removed from over the stent 102 by retracting proximally the hemostatic valve assembly 112 after loosening the threaded cap 116 and pulling it proximally until the cap 116 is in registration with the marker 126 to assure that the sheath has cleared the stent 102.

As soon as this has been accomplished, the inner balloon 22 can be inflated by opening the valve assembly 72 and leaving the valve assembly 73 closed and supplying an inflation medium to the inner balloon 22 to expand the stent 102 radially and outwardly to increase the size of the opening or flow passage through the stenosis. If it is desired to further increase the size of the opening in the stenosis, the outer balloon 23 can then be inflated by opening of the valve 73 and supplying additional inflation medium to the manifold assembly 51 to inflate the outer balloon 23 and to carry with it and expand the stent 102 to further increase the size of the opening through the stenosis. As soon as it has been established that the stent 102 has been fully expanded to the desired diameter and embedded in the vessel wall, the balloons 21, 22 and 23 can be deflated by withdrawing inflation medium from the same. The entire multiple balloon stent delivery catheter 101 along with the guide wire 68 can then be removed from the femoral artery and the femoral artery closed surgically in a conventional manner.

It should be appreciated that in connection with the multiple balloon catheter 11 and the multiple balloon stent delivery catheter 101, that the distal balloon 21 can have any appropriate size. For example, it can be a small size balloon as hereinbefore described or, if desired, it can be a larger size balloon substantially the same size as the outer balloon 23.

It also should be appreciated that in place of one distal balloon 21, a plurality of distal balloons can be provided which are disposed in tandem, as for example as shown in FIG. 11 in which another distal balloon 21a proximal of the other distal balloon 21 has been provided in the multiple balloon catheter 136. An additional marker 37a has been provided in the balloon 21a.

Another multiple balloon catheter 141 incorporating the present invention is shown in FIG. 12 in which a stepped outer coaxial balloon 23a is provided having a distal extremity of lesser diameter than the proximal extremity of the balloon 23a. The proximal and distal portions of the balloon 23a can be of various lengths as desired.

In connection with the foregoing embodiments it also should be appreciated that the balloons provided on the multiple balloon catheters 11 and 101 can have various configurations. Thus, for example, as shown in FIG. 13, the outer balloon 23b can be in the form of a tapered balloon having a taper which gradually decreases in a distal direction.

The balloon catheters 11 and 101 are high pressure substantially non-distensible balloons which can be distended at highly controlled and predictable rates. The balloons can be of various sizes ranging from 1 to 8 millimeters in diameter and 10 to 40 millimeters in length. The balloons can have various profiles, as for example straight, tapered, center or ends bulging portions. The catheters can be formed for over-the-wire use or can be provided with a fixed guide wire. The distal balloon can be utilized for maintaining an anatomical position for the catheter while other functions are being performed with the catheter, as for example deployment of a stent as hereinbefore described.

Various methods can be performed utilizing the multiple balloon catheter hereinbefore described. First it should be appreciated that the multiple balloon catheter can be utilized for delivering a stent without having a sheath covering the stent when that is desired as for example for purposes of economy. The method of the present invention can be utilized with a multiple balloon stent delivery catheter which has an outer coaxial balloon which is a stepped balloon having proximal and distal portions with the distal portion having a diameter less than the diameter of the proximal portion. The stent can be mounted on the distal portion of smaller diameter. When this is the case, the sheath can be withdrawn to uncover the stent while still covering the proximal portion of the outer coaxial balloon. Thereafter, the outer coaxial balloon can be inflated to cause expansion of the uncovered distal portion to cause deployment of the stent. Alternatively, the stent can be mounted on the proximal portion of larger diameter and covered by the sheath. The distal portion of smaller diameter can then be advanced into the stenosis and can be utilized for predilating the stenosis. The outer coaxial balloon can then be delated and the catheter advanced so that the proximal portion of larger diameter with the stent thereon can be moved into the stenosis through the larger flow passage formed in inflation of the distal portion. Thereafter, the sheath can be withdrawn and the proximal portion of the distal balloon can be inflated to deploy the stent. The method can be utilized in a similar manner with the tapered outer coaxial balloon with the stent being carried by the tapered outer balloon and being advanced into the stenosis. The sheath can be withdrawn to uncover the stent after which the balloon can be inflated to deploy the stent.

Although the stent delivery catheter of the present invention has been described for delivering a single stent at a time, it should be appreciated that a plurality of shorter segmented stents all mounted on a balloon and, if necessary, on a longer balloon and then deployed as hereinbefore described to treat longer lesions or a plurality of lesions in a vessel.

Although the present multiple balloon catheter has been described principally as a stent delivery catheter, it should be appreciated that it also can be utilized for dilating one or more stenoses in a vessel. This can be readily accomplished by deploying the catheter into the vessel as hereinbefore described and then advancing the distal balloon into a stenosis and dilating that stenosis to increase the size of the flow passage therethrough. The distal balloon can be then deflated and the catheter advanced to advance the coaxial outer and inner balloons into registration with the stenosis after which at least one of the inner and outer balloons can be inflated to increase the size of the flow passage in the stenosis. Alternatively, the inner coaxial balloon can be inflated followed by inflation of the outer coaxial balloon when a larger size flow passage is desired through the stenosis. It should be appreciated that if there are additional stenoses in the same vessel, the multiple balloons can be further advanced into the vessel to perform the same dilating procedure with additional stenoses in the vessel.

Although the catheters 11 and 101 have been described principally in connection with angioplasty procedures involving stenoses in vessels of the heart, it should be appreciated that the teaching herein is equally applicable to procedures in carotid arteries and other vessels in the human body.

We claim:

1. A multiple balloon catheter for use in a vessel of a patient and for use with an inflation/deflation device comprising a flexible elongate tubular member having proximal and distal extremities, a distal balloon mounted on the distal extremity of the flexible elongate tubular member, coaxial inner and outer balloons mounted on the distal extremity of the flexible elongate member proximal of the distal balloon, said flexible elongate tubular member having balloon inflation lumens therein in communication with the interiors of the distal balloon and the inner and outer coaxial balloons and a manifold secured to the proximal extremity of the flexible elongate tubular member in communication with the inflation lumens and adjusted to be coupled to the inflation/deflation device and valve means carried by the inflation/deflation manifold for inflating the distal balloon and the inner and outer coaxial balloons one at a time or in unison without removal of the inflation/deflation device from the manifold.

2. A catheter as in claim 1 further comprising an expandable stent carried by the outer balloon, a protective sheath overlying the stent extending from the stent to the proximal extremity of the flexible elongate tubular member and means secured to the sheath for removing the sheath proximally to clear the stent.

3. A catheter as in claim 2 wherein said means for removing the stent includes means for introducing a fluid into an annular space between the sheath and the flexible elongate tubular member.

4. A catheter as in claim 2 wherein said means for removing the sheath includes a hemostasis valve assembly, said hemostasis valve assembly including a port for introducing a fluid into an annular space between the sheath and the flexible elongate tubular member.

5. A catheter as in claim 1 wherein said inflation manifold further comprises ganged valve assemblies movable between open and closed positions.

6. A catheter as in claim 4 further comprising a marker carried by the proximal extremity of the flexible elongate tubular member and spaced a predetermined distance from the hemostasis valve assembly when the sheath overlies the stent to provide a gauge visible to the human eye to designate the distance the hemostasis valve assembly must be retracted to uncover the stent.

7. A catheter as in claim 1 wherein said outer balloon has a tapered configuration.

8. A catheter as in claim 1 wherein said outer balloon has a stepped configuration.

9. A catheter as in claim 1 further including an additional distal balloon proximal of the distal balloon and distal of the coaxial inner and outer balloons.

10. A catheter as in claim 1 further comprising a stent carried by the coaxial inner and outer balloons.

11. A multiple balloon stent delivery catheter comprising a flexible elongate tubular member having proximal and distal extremities, a distal balloon mounted on the distal extremity of the flexible elongate tubular member, coaxial inner and outer balloons mounted on the distal extremity of the flexible elongate member proximal of the distal balloon, the flexible elongate tubular member being formed with balloon inflation lumens in communication with the interiors of the distal balloon and the inner and outer balloons, a stent carried by the outer balloon, a sheath having proximal extremity and overlying the stent and extending proximally of the stent to the proximal extremity of the flexible elongate tubular member and an attachment secured to the proximal extremity of the sheath for facilitating withdrawing the sheath to uncover the stent.

12. A catheter as in claim 11 further comprising a first radiopaque marker carried by the distal extremity of the flexible elongate member and being disposed substantially equidistant from the ends of the distal balloon, second and third radiopaque markers carried by the distal extremity of the flexible elongate tubular member spaced apart within the confines of the inner balloon whereby the position of the inner balloon can be distinguished from that of the position of the distal balloon.

13. A catheter as in claim 11 further comprising a marker visible to the human eye carried by the proximal extremity of the flexible elongate tubular member and providing a visual indication of the distance the sheath must be retracted in order to uncover the stent.

\* \* \* \* \*